US00PP16799P2

(12) United States Plant Patent
Verwer

(10) Patent No.: US PP16,799 P2
(45) Date of Patent: Jul. 11, 2006

(54) ***DAHLIA* PLANT NAMED 'MELODY ALLEGRO'**

(50) Latin Name: *Dahlia hybrida*
Varietal Denomination: Melody Allegro

(75) Inventor: Aad W. M. Verwer, Lisse (NL)

(73) Assignee: Verwer Dahlias B.V., Lisse (NL)

( * ) Notice: Subject to any disclaimer, the term of this patent is extended or adjusted under 35 U.S.C. 154(b) by 16 days.

(21) Appl. No.: 11/118,994

(22) Filed: Apr. 30, 2005

(51) Int. Cl.
*A01H 5/00* (2006.01)

(52) U.S. Cl. ..... Plt./321

(58) Field of Classification Search ..... Plt./321
See application file for complete search history.

*Primary Examiner*—Kent Bell
(74) *Attorney, Agent, or Firm*—C. A. Whealy

(57) ABSTRACT

A new and distinct cultivar of *Dahlia* plant named 'Melody Allegro', characterized by its upright and outwardly spreading plant habit; freely branching growth habit; early and freely flowering habit; decorative inflorescence form; large inflorescences with salmon pink-colored ray florets; and good postproduction longevity and garden performance.

2 Drawing Sheets

Botanical designation: *Dahlia hybrida.*
Cultivar denomination: 'Melody Allegro'.

BACKGROUND OF THE INVENTION

The present Invention relates to a new and distinct cultivar of *Dahlia* plant, botanically known as *Dahlia hybrida* and hereinafter referred to by the name 'Melody Allegro'.

The new *Dahlia* is a product of a planned breeding program conducted by the Inventor in Lisse, The Netherlands. The objective of the breeding program is to create new potted *Dahlia* cultivars with compact plant habit, freely branching growth habit, early and freely flowering habit, decorative inflorescence form, attractive ray floret coloration, and good postproduction longevity and garden performance.

The new *Dahlia* originated from a cross pollination made by the Inventor in 2000 of a proprietary selection of *Dahlia hybrida* identified as code number Vd-0-93, not patent, as the female, or seed, parent with the *Dahlia hybrida* cultivar Tout à Toi, not patented, as the male, or pollen, parent. The new *Dahlia* was discovered and selected by the Inventor as a single flowering plant within the progeny of the stated cross pollination grown in a controlled environment in Lisse, The Netherlands, during the summer of 2001.

Asexual reproduction of the new *Dahlia* by cuttings was first conducted in Lisse, The Netherlands during the spring of 2002. Asexual reproduction by cuttings has shown that the unique features of this new *Dahlia* are stable and reproduced true to type in successive generations.

SUMMARY OF THE INVENTION

The cultivar Melody Allegro has not been observed under all possible environmental conditions. The phenotype may vary somewhat with variations in environment such as temperature and light intensity without, however, any variance in genotype.

The following traits have been repeatedly observed and are determined to be the unique characteristics of 'Melody Allegro'. These characteristics in combination distinguish 'Melody Allegro' as a new and distinct *Dahlia* cultivar:

1. Upright and outwardly spreading plant habit.
2. Freely branching growth habit.
3. Early and freely flowering habit.
4. Decorative inflorescence form.
5. Large inflorescences with salmon pink-colored ray florets.
6. Good postproduction longevity and garden performance.

Plants of the new *Dahlia* differ primarily from plants of the female parent selection in the following characteristics:

1. Plants of the new *Dahlia* are taller than plants of the female parent selection.
2. Plants of the new *Dahlia* and the female parent selection differ in inflorescence form.
3. Plants of the new *Dahlia* and the female parent selection differ in ray floret coloration.

Plants of the new *Dahlia* differ primarily from plants of the male parent, the cultivar Tout à Toi, in the following characteristics:

1. Plants of the new *Dahlia* are shorter than plants of the cultivar Tout à Toi.
2. Plants of the new *Dahlia* are more freely branching than plants of the cultivar Tout à Toi.
3. Plants of the new *Dahlia* flower earlier than plants of the cultivar Tout à Toi.
4. Plants of the new *Dahlia* have more ray florets per inflorescence than plants of the cultivar Tout à Toi.
5. Plants of the new *Dahlia* and the cultivar Tout à Toi differ in inflorescence form.

Plants of the new *Dahlia* can be compared to plants of the cultivar Melody Dixie, disclosed in U.S. Plant Pat. No. 12,911. In side-by-side comparisons conducted in Lisse, The Netherlands, plants of the new *Dahlia* differed from plants of the cultivar Melody Dixie in the following characteristics:

1. Plants of the new *Dahlia* were more outwardly spreading than plants of the cultivar Melody Dixie.
2. Plants of the new *Dahlia* has darker green-colored leaves than plants of the cultivar Melody Dixie.
3. Ray floret color of plants of the new *Dahlia* was salmon pink whereas ray floret color of plants of the cultivar Melody Dixie was purple.

BRIEF DESCRIPTION OF THE PHOTOGRAPHS

The accompanying colored photographs illustrate the overall appearance of the new *Dahlia* showing the colors as true as it is reasonably possible to obtain in colored reproductions of this type. Colors in the photographs may differ from the color values cited in the detailed botanical description which accurately describe the colors of the new *Dahlia*.

The photograph on the first sheet comprises a side perspective view of a typical flowering plant of 'Melody Allegro'.

The photograph on the second sheet is a close-up view of a typical inflorescence of 'Melody Allegro'.

DETAILED BOTANICAL DESCRIPTION

In the following description, color references are made to The Royal Horticultural Society Colour Chart, 1995 Edition, except where general terms of ordinary dictionary significance are used. The aforementioned photograph and the following observations and measurements describe plants grown and flowered during the summer and early autumn in Lisse, The Netherlands, in an outdoor nursery and under conditions which approximate those generally used in commercial production. During the production of the plants, day temperatures ranged between 15 and 30° C. and night temperatures ranged between 10 and 20° C. Plants were pinched one time about three weeks after planting rooted cuttings. Plants were about four months old when the photographs and the description were taken.

Botanical classification: *Dahlia hybrida* cultivar Melody Allegro.

Parentage:

*Female, or seed, parent.*—Proprietary selection of *Dahlia hybrida* identified as code number Vd-0-93, not patented.

*Male, or pollen, parent.*—*Dahlia hybrida* cultivar Tout à Toi, not patented.

Propagation:

*Type.*—By vegetative cuttings.

*Time to initiate roots.*—Summer and winter: About 5 days at 17° C.

*Time to produce a rooted young plant.*—Summer: About 14 days at 17° C. Winter: About 17 days at 17° C.

*Root description.*—Fine, fibrous and well-branched; older roots, fleshy.

*Tuber description.*—Shape: Fusiform. Clump diameter: About 25 cm. Color: Close to 199C.

Plant description:

*Appearance.*—Perennial decorative-type potted *Dahlia*. Upright and outwardly spreading plant habit. Freely branching habit, about eight basal branches each with about six lateral branches develop after pinching; dense and full plants. Moderately vigorous growth habit.

*Plant height.*—About 60 cm.

*Plant diameter.*—About 50 cm.

*Lateral branch description.*—Length: About 40 cm. Diameter: Towards base: About 1.1 cm. Towards apex: About 3 mm. Internode length: About 5 to 11 cm. Strength: Strong. Texture: Glabrous, smooth. Color: 146C; towards the apex, blushed with 166A.

*Foliage description.*—Arrangement: Leaves opposite; leaves may be single or compound with three or five leaflets. Shape: Ovate. Apex: Aristate. Base: Attenuate. Margin: Serrate; sinuses divergent. Length: Single leaves: About 9 cm. Compound leaves with three leaflets: About 15 cm. Compound leaves with five leaflets: About 21 cm. Width: Single leaves: About 5 cm. Compound leaves with three leaflets: About 13 cm. Compound leaves with five leaflets: About 17 cm. Venation pattern: Pinnate. Texture, upper and lower surfaces: Smooth, glabrous. Color: Developing foliage, upper surface: 137A. Developing foliage, lower surface: 191A. Fully expanded foliage, upper surface: Darker than 137A. Fully expanded foliage, lower surface: 191A. Venation, upper surface: 146A. Venation, lower surface: 147C. Petiole length: About 1.2 to 5 cm. Petiole diameter: About 2.3 mm. Petiole color, upper surface: 137A. Petiole color, lower surface: Lighter than 151A.

Inflorescence description:

*Appearance.*—Decorative inflorescence form; inflorescences roughly hemispherical in profile. Inflorescences borne on terminals, arising from leaf axils, positioned above the foliage. Ray and disc florets develop acropetally on the receptacle. Inflorescences not fragrant. Inflorescences persistent.

*Flowering response.*—Flowering recurrent to continuous during the summer and autumn in The Netherlands. Plants start flowering about 60 days after planting.

*Postproduction longevity.*—On the plant, inflorescences maintain good color and substance for about 30 days in an outdoor environment. As cut flowers, inflorescences maintain good color and substance for about six days in an indoor environment.

*Quantity of inflorescences per flowering stem.*—About five open inflorescences and about five inflorescence buds per stem; about 30 to 40 inflorescences per plant.

*Inflorescence size.*—Diameter: About 11 cm. Depth (height): About 6 cm. Diameter of disc: About 4 mm. Receptacle diameter: About 2.1 cm. Receptacle height: About 1.5 cm.

*Inflorescence buds.*—Length: About 1.4 cm. Diameter: About 1.9 cm. Shape: Oblate. Color: Towards the apex, 151A; towards the base, 141A.

*Ray florets.*—Length, fully developed: About 4.1 cm. Width, fully developed: About 2 cm. Orientation: Initially upright, outer florets perpendicular to the peduncle to reflexed. Shape: Ovate. Aspect: Longitudinal axis concave. Apex: Rounded, retuse or acute. Base: Fused. Margin: Entire. Texture, upper and lower surfaces: Smooth, glabrous. Number of ray florets per inflorescence: About 170 arranged in about 21 rows. Venation pattern: Parallel. Color: When opening, upper surface: 59B; towards the base, 1B. When opening, lower surface: 181A; towards the base, 1A. Fully opened, upper surface: 1D blushed with 168C; mid-section, 169A; towards the base, 1B. Fully opened, lower surface: 169A; towards the margins, 168A; longitudinal ribs, 63B.

*Disc florets.*—Number of disc florets per inflorescence: About 12. Shape: Tubular, elongated. Apex: Five-pointed. Base: Attenuate. Length: About 9 mm. Width: At the apex, about 1 mm; at the base, about 0.5 mm. Color: Immature: 154C. Mature: Apex: 3A. Mid-section and base: 154C.

*Phyllaries.*—Quantity: One whorl with about ten phyllaries. Shape: Ovate to lanceolate. Apex: Acute. Base: Attenuate. Margin: Entire. Length: About 2.1 cm. Width: About 6 mm. Texture, upper and lower surfaces: Smooth, glabrous; leathery. Color, upper surface: 152B. Color, lower surface: Close to 146C.

*Peduncles.*—Length: About 12 cm. Diameter: About 5 mm. Angle: About 10° from vertical. Strength: Strong. Texture: Glabrous, smooth. Color: 146C blushed with 183A.

*Reproductive organs.*—Androecium: Present on disc florets only. Stamen quantity: About five per floret. Anther shape: Linear. Anther length: About 4 mm. Anther color: 1D. Pollen amount: Scarce. Pollen color: 21B. Gynoecium: Present on ray and disc florets. Pistil quantity: One per floret. Pistil length: About 5 mm. Stigma shape: Lanceolate. Stigma color: 6C. Style length: About 3 mm. Style color: 1C. Ovary color: 2D.

*Seeds/fruits.*—Seed and fruit development has not been observed.

Disease/pest resistance: Resistance to pathogens and pests common to *Dahlias* has not been observed on plants grown under commercial greenhouse or outdoor conditions.

Weather tolerance: Plants of the new *Dahlia* have been observed to be very tolerant to wind, rain and full sun conditions. Plants of the new *Dahlia* have been observed to tolerate temperatures from 0 to 40° C.

It is claimed:

1. A new and distinct cultivar of *Dahlia* plant named 'Melody Allegro', as illustrated and described.

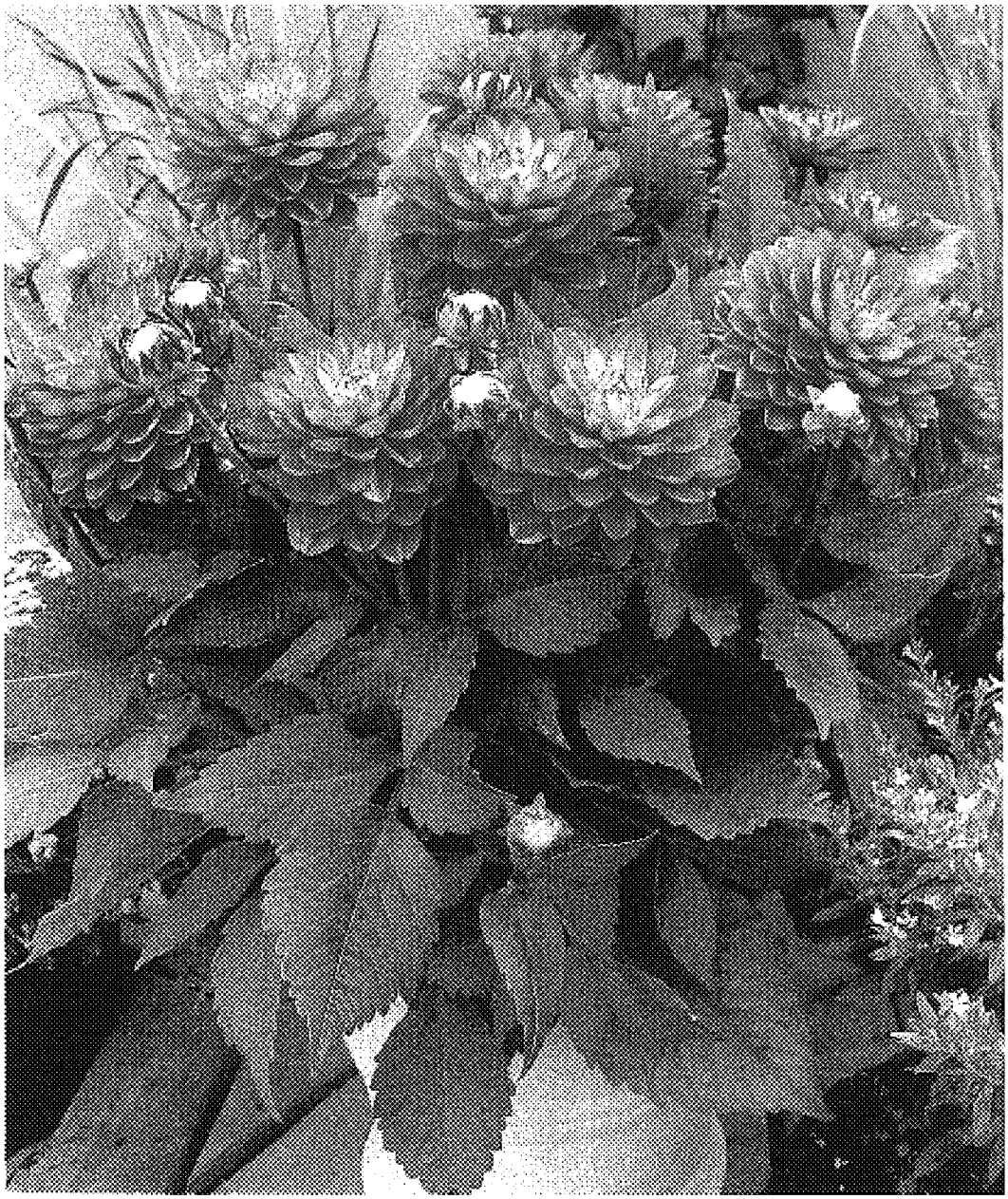

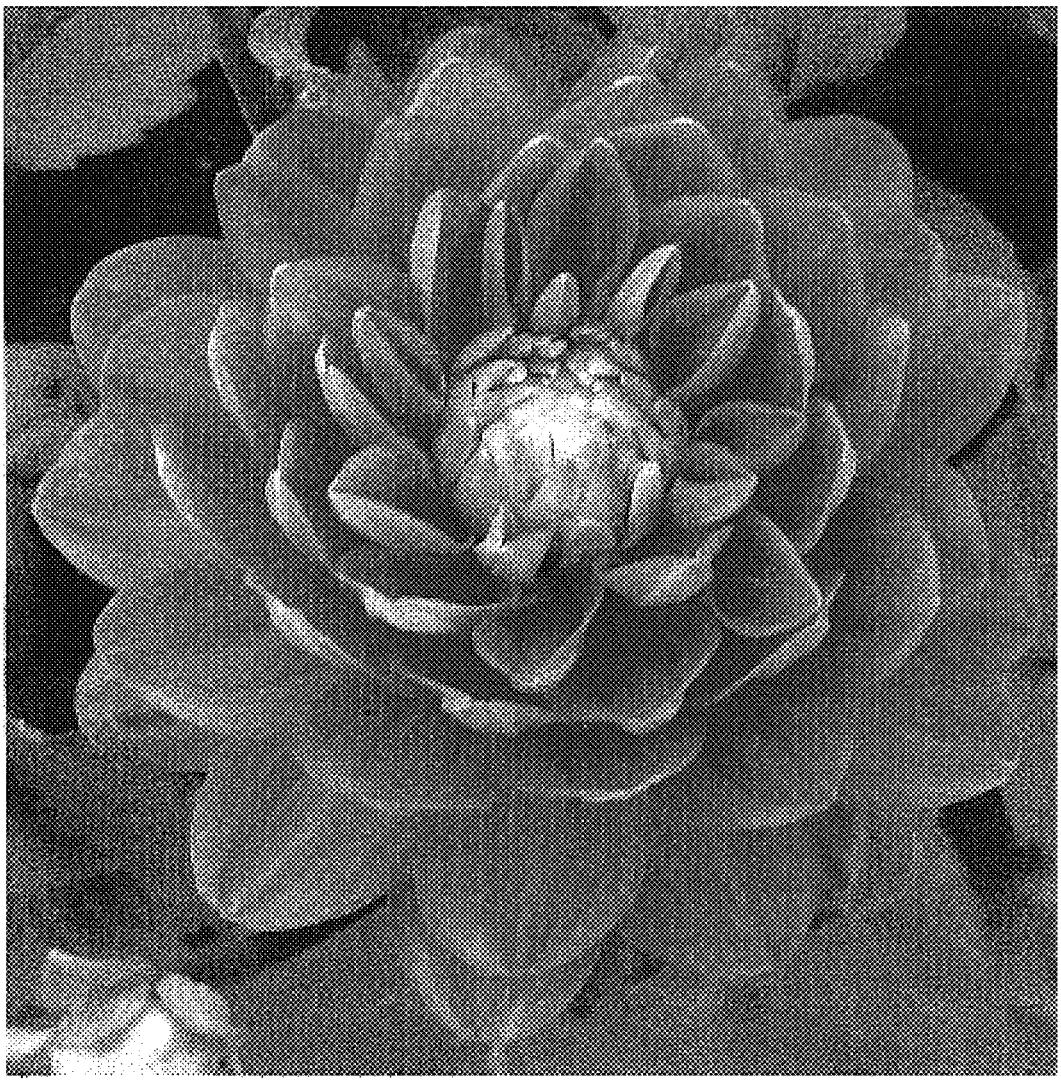

* * * * *